(12) United States Patent
Biemans et al.

(10) Patent No.: US 9,695,128 B2
(45) Date of Patent: Jul. 4, 2017

(54) ETHYNYL DERIVATIVES

(71) Applicant: Hoffmann-La Roche Inc., Little Falls, NJ (US)

(72) Inventors: Barbara Biemans, Basel (CH); Wolfgang Guba, Muellheim (DE); Georg Jaeschke, Basel (CH); Antonio Ricci, Biel-Benken (CH); Daniel Rueher, Raedersdorf (FR); Eric Vieira, Frenkendorf (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/205,466

(22) Filed: Jul. 8, 2016

(65) Prior Publication Data

US 2017/0008854 A1 Jan. 12, 2017

Related U.S. Application Data

(63) Continuation of application No. PCT/EP2015/050127, filed on Jan. 7, 2015.

(30) Foreign Application Priority Data

Jan. 10, 2014 (EP) .................................. 14150700

(51) Int. Cl.

| | | |
|---|---|---|
| *C07D 233/74* | (2006.01) | |
| *C07D 498/04* | (2006.01) | |
| *C07D 487/14* | (2006.01) | |
| *C07D 471/04* | (2006.01) | |
| *C07D 491/107* | (2006.01) | |
| *C07D 233/64* | (2006.01) | |
| *C07D 401/04* | (2006.01) | |

(52) U.S. Cl.
CPC ......... *C07D 233/74* (2013.01); *C07D 233/64* (2013.01); *C07D 401/04* (2013.01); *C07D 471/04* (2013.01); *C07D 487/14* (2013.01); *C07D 491/107* (2013.01); *C07D 498/04* (2013.01)

(58) Field of Classification Search
CPC .. C07D 233/74; C07D 498/04; C07D 487/14; C07D 471/04; C07D 491/07; C07D 491/107
See application file for complete search history.

(56) References Cited

U.S. PATENT DOCUMENTS

2012/0245153 A1 9/2012 Conn et al.

FOREIGN PATENT DOCUMENTS

| WO | 2011/029104 A1 | 3/2011 |
|---|---|---|
| WO | 2011/128279 A1 | 10/2011 |
| WO | 2012/162635 A1 | 11/2012 |

OTHER PUBLICATIONS

IPRP for PCT/EP2015/050127 (WO2015104271).

*Primary Examiner* — Kahsay Habte
(74) *Attorney, Agent, or Firm* — Tamara A. Kale

(57) ABSTRACT

The present invention relates to compounds of formula I

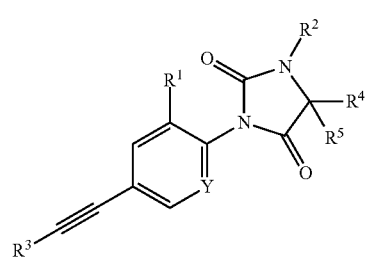

having variables as described herein, which are useful for the treatment of Parkinson's disease, anxiety, emesis, obsessive compulsive disorder, autism, neuroprotection, cancer, depression and diabetes type 2.

8 Claims, 1 Drawing Sheet

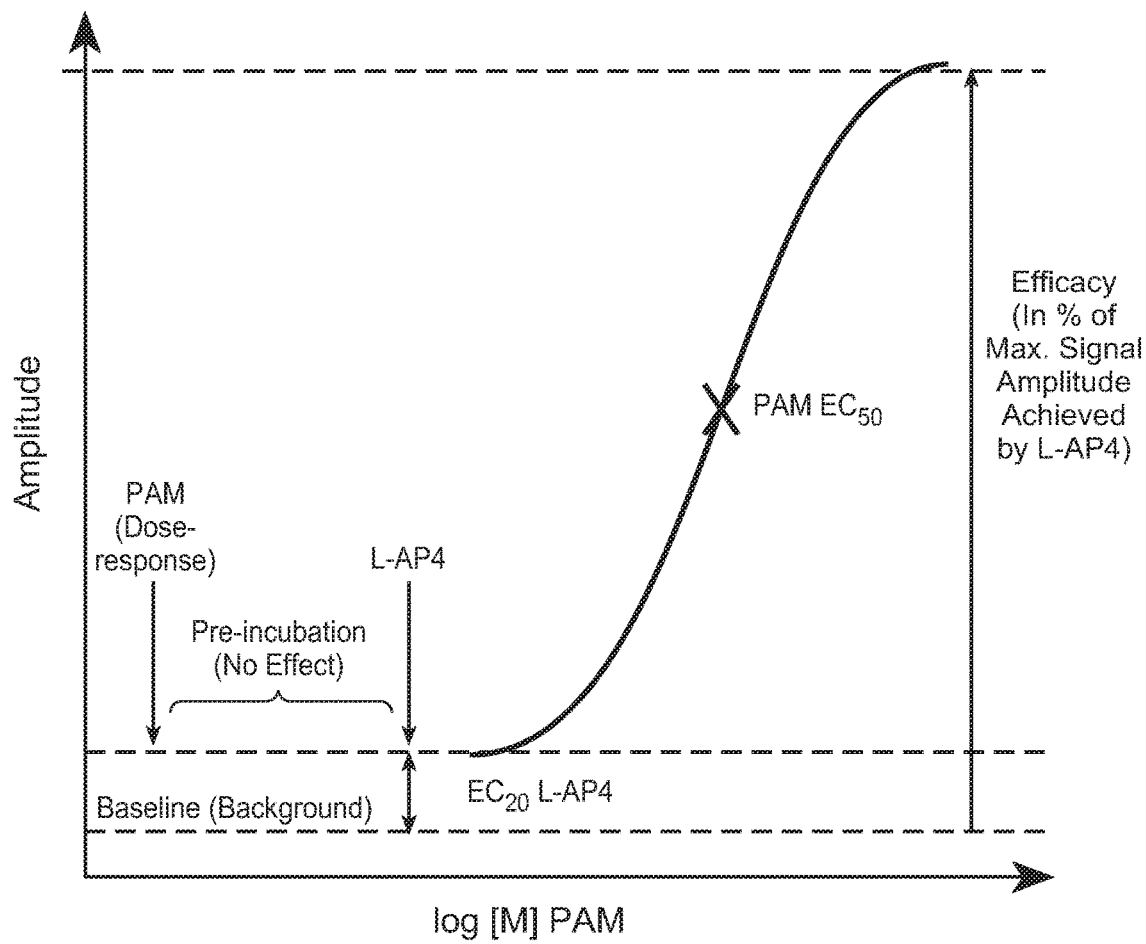

ETHYNYL DERIVATIVES

This application is a continuation of International Application PCT/EP2015/050127, filed Jan. 7, 2015, which claims benefit of priority to European Application 14150700.4, filed Jan. 10, 2014, each of which is incorporated herein by reference in its entirety.

The present invention relates to compounds of formula I

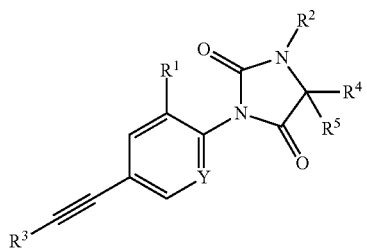

wherein
Y is C—$R^{1'}$;
$R^{1'}$ is hydrogen or halogen;
$R^1$ is hydrogen or halogen;
$R^2$ is hydrogen, lower alkyl or phenyl;
$R^4$ is hydrogen or lower alkyl;
or $R^2$ and $R^4$ may form together with the corresponding atoms, to which they are attached the following rings

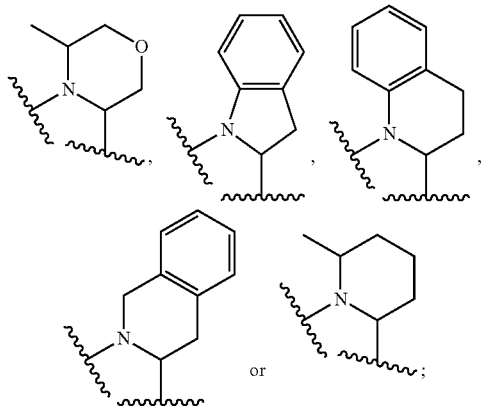

$R^5$ is hydrogen or lower alkyl; and if $R^2$ and $R^4$ form a ring as described above, than $R^5$ is hydrogen; or
$R^4$ and $R^5$ may form together with the C-atom to which they are attached a heterocycloalkyl ring;
$R^3$ is phenyl or pyridinyl, wherein the N atom in the pyridinyl group may be in different positions;
or to a pharmaceutically acceptable salt or acid addition salt, to a racemic mixture, or to its corresponding enantiomer and/or optical isomer and/or stereoisomer thereof.

It has been surprisingly been found that the compounds of general formula I are positive allosteric modulators (PAMs) of metabotropic glutamate receptor 4 (mGluR4).

Metabotropic glutamate receptor 4 is a protein that in humans is encoded by the GRM4 gene.

Together with GRM6, GRM7 and GRM8 it belongs to group III of the Metabotropic glutamate receptor family, and is negatively coupled to adenylate cyclase via activation of the Gαi/o protein. It is expressed primarily on presynaptic terminals, functioning as an autoreceptor or heteroceptor and its activation leads to decreases in transmitter release from presynaptic terminals. mGluR4 is currently receiving much attention based primarily upon its unique distribution and the recent evidence that activation of this receptor plays key modulatory role in many CNS and non-CNS pathways (Celanire S, Campo B, *Expert Opinion in Drug Discovery*, 2012)

The similarity in the ligand binding domains of group III mGluRs creates a challenge for identifying selective orthosteric agonists of this receptor, although some progress has been made in this area. However, targeting positive allosteric modulators (PAMs) rather than orthosteric agonists provides a broader opportunity to identify molecules that are exclusively selective between mGluRs.

mGluR4 PAM is emerging as a promising target for the treatment of motor (and non motor) symptoms as well as a disease-modifying agent in Parkinson's disease through a non-dopaminergic approach.

Parkinson's disease is a progressive neurodegenerative disease that results in the loss of dopaminergic neurons in the substantia nigra (SN). One consequence of the depletion of dopamine in this disease is a series of movement disorders, including bradykinesia, akinesia, tremor, gait disorders and problems with balance. These motor disturbances form the hallmark of PD, although there are many other non-motor symptoms that are associated with the disease. Early in the course of the disease, PD symptoms are effectively treated by dopamine replacement or augmentation, with the use of dopamine D2 receptor agonists, levodopa or mono-amine oxidase B inhibitors. However, as the disease progresses these agents become less effective in controlling motor symptoms. Additionally, their use is limited by the emergence of adverse effects including dopamine agonist-induced dyskinesias. Consequently, there remains a need for new approaches to the treatment of PD that improve the effectiveness of the control of motor symptoms.

Activation of metabotropic glutamate receptor 4 (mGluR4) has been proposed as a potential therapeutic approach to Parkinson's disease. A member of the group III mGluRs, mGluR4 is predominantly a presynaptic glutamate receptor that is expressed in several key locations in the basal ganglia circuits that control movement. Activation of mGluR4 with group III-preferring agonists decreases inhibitory and excitatory post synaptic potentials, presumably by decreasing the release of GABA and glutamate respectively.

The search for novel drugs that relieve motor symptoms of Parkinsonism whilst attenuating the ongoing degeneration of nigrostriatal neurons is of particular interest. Orthosteric mGluR4 agonist L-AP4 has demonstrated neuroprotective effects in a 6-OHDA rodent model of PD and first positive allosteric modulator (−)-PHCCC reduced nigrostriatal degeneration in mice treated with 1-Methyl-4-Phenyl-1,2,3,6-Tetrahydropyridine (MPTP). Those studies provide preclinical evidence suggesting that mGluR4 activators constitute a strong approach not only for symptomatic treatments of PD, but also potentially as disease modifiers.

The neuroprotective effect of selective mGluR4 agonists was also described in *Neuroreport*, 19(4), 475-8, 2008, *Proc. Natl. Acad. Sci, USA*, 100(23), 13668-73, 2003 and *J. Neurosci.* 26(27), 7222-9, 2006 and *Mol. Pharmacol.* 74(5), 1345-58, 2008.

Anxiety disorders are among the most prevalent psychiatric disorders in the world, and are co-morbid with Parkinson's disease (Prediger R, et al. *Neuropharmacology* 2012; 62:115-24). Excessive glutamatergic neurotransmission is one important feature of anxiety pathophysiology. Based on presynaptic localization of mGluR4 in brain areas involved in anxiety and mood disorders, and dampening excessive brain excitability, the mGluR4 activators may represent a new generation of anxiolytic therapeutics (*Eur. J. Pharmacol.*, 498(1-3), 153-6, 2004).

Addex has reported in 2010 that ADX88178 was active in two preclinical rodent models of anxiety: the marble burying test in mice and EPM in mice and rats. ADX88178 also displayed an anxiolytic-like profile in the rat EPM test after oral dosing.

mGluR4 modulators were also shown to exert anti-depressive actions (*Neuropharmacology*, 46(2), 151-9, 2004).

In addition, mGluR4 were also shown to be involved in glucagon secretion inhibition (*Diabetes*, 53(4), 998-1006, 2004). Therefore, orthosteric or positive allosteric modulators of mGluR4 have potential for the treatment of type 2 diabetes through its hypoglycemic effect.

Moreover, mGluR4 was shown to be expressed in prostate cancer cell-line (*Anticancer Res.* 29(1), 371-7, 2009) or colorectal carcinoma (*Cli. Cancer Research*, 11(9)3288-95, 2005). mGluR4 modulators may therefore have also potential role for the treatment of cancers.

In addition, in *British Journal of Pharmacology* (2013), 169, 1824-1839 agonists of mGluR4 may further be used in the treatment of positive, negative and cognitive symptoms of schizophrenia.

Other proposed effects of mGluR4 PAM's can be expected for the treatment of emesis, obsessive compulsive disorder and autism.

Compounds of formula I are distinguished by having valuable therapeutic properties. They can be used in the treatment or prevention of disorders, relating to allosteric modulators for the mGluR4 receptor.

The most preferred indications for compounds which are allosteric modulators for the mGluR4 receptor are Parkinson's disease, anxiety, emesis, obsessive compulsive disorder, autism, neuroprotection, cancer, depression, schizophrenia and type 2 diabetes.

The present invention relates to compounds of formula I and to their pharmaceutically acceptable salts, to these compounds as pharmaceutically active substances, to the processes for their production as well as to the use in the treatment or prevention of disorders, relating to allosteric modulators for the mGluR4 receptor, such as Parkinson's disease, anxiety, emesis, obsessive compulsive disorder, anorexia, autism, neuroprotection, cancer, depression, schizophrenia and diabetes type 2 and to pharmaceutical compositions containing the compounds of formula I.

A further object of the present invention is a method for the treatment or prophylaxis of Parkinson's disease, anxiety, emesis, obsessive compulsive disorder, autism, neuroprotection, cancer, depression, schizophrenia and type 2 diabetes, which method comprises administering an effective amount of a compound of formula I to a mammal in need.

Furthermore, the invention includes all racemic mixtures, all their corresponding enantiomers and/or optical isomers.

The following definitions of the general terms used in the present description apply irrespective of whether the terms in question appear alone or in combination.

The following definitions of the general terms used in the present description apply irrespective of whether the terms in question appear alone or in combination.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "cycloalkyl" denotes a saturated ring containing from 3 to 7 carbon atoms, for example cyclopropyl, cyclobutyl, cyclopentyl, cyclohexyl or cycloheptyl.

The term heterocycloalkyl" denoted a cycloalkyl ring as defined above, wherein at least one carbon atom is replaced by O, N, or S, for example tetrahydrofuranyl, morpholinyl piperidinyl or oxetanyl.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

BRIEF DESCRIPTION OF THE DRAWING

FIG. 1: Illustration of the experimental outline for mGlu4 PAM $Ca^{2+}$ mobilization screening assay and the determination of $EC_{50}$ and % Emax values.

One embodiment of the invention are compounds of formula I,

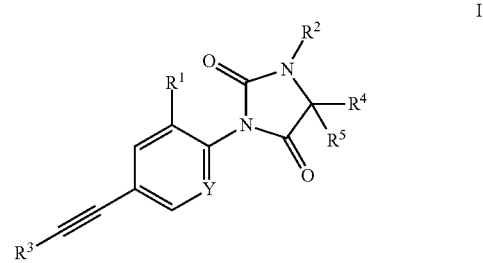

wherein
Y is C—$R^{1'}$;
$R^{1'}$ is hydrogen or halogen;
$R^1$ is hydrogen or halogen;
$R^2$ and $R^4$ form together with the corresponding atoms, to which they are attached
the following rings

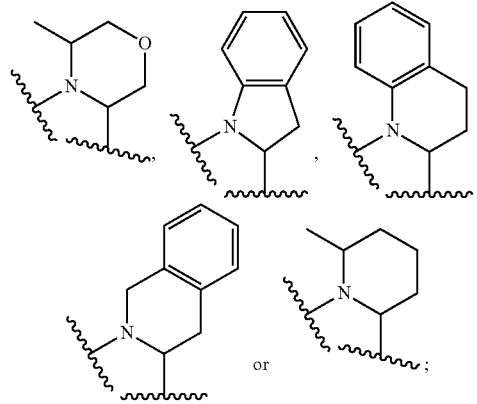

$R^5$ is hydrogen or
$R^4$ and $R^5$ may form together with the C-atom to which they are attached a heterocycloalkyl ring;
$R^3$ is phenyl or pyridinyl, wherein the N atom in the pyridinyl group may be in different positions;

or a pharmaceutically acceptable salt or acid addition salt, a racemic mixture, or its corresponding enantiomer and/or optical isomer and/or stereoisomer thereof.

Examples include the following:
(5RS,8aRS)-2-[2,6-difluoro-4-(2-phenylethynyl)phenyl]-5-methyl-5,6,8,8a-tetrahydroimidazo[5,1-c][1,4]oxazine-1,3-dione
(3aRS)-2-[2,6-difluoro-4-(2-phenylethynyl)phenyl]-3a,4-dihydroimidazo[1,5-a]indole-1,3-dione
(3aRS)-2-[2,6-difluoro-4-(2-phenylethynyl)phenyl]-4,5-dihydro-3aH-imidazo[1,5-a]quinoline-1,3-dione
(10aRS)-2-[2,6-difluoro-4-(2-phenylethynyl)phenyl]-10,10a-dihydro-5H-imidazo[1,5-b]isoquinoline-1,3-dione
(5RS,8aRS)-2-[2-chloro-4-(2-phenylethynyl)phenyl]-5-methyl-6,7,8,8a-tetrahydro-5H-imidazo[1,5-a]pyridine-1,3-dione or
(5RS,8aRS)-2-[2-chloro-6-fluoro-4-[2-(3-pyridyl)ethynyl]phenyl]-5-methyl-6,7,8,8a-tetrahydro-5H-imidazo[1,5-a]pyridine-1,3-dione.

One further embodiment of the present invention are compounds of formula I, wherein

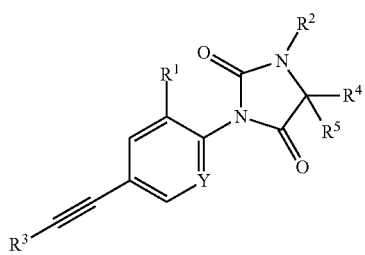

I wherein
Y is C—R¹';
R¹' is hydrogen or halogen;
R¹ is hydrogen or halogen;
R² is hydrogen, lower alkyl or phenyl;
R⁴ is hydrogen or lower alkyl;
R⁵ is hydrogen or lower alkyl; or
R⁴ and R⁵ may form together with the C-atom to which they are attached a heterocycloalkyl ring;
R³ is phenyl or pyridinyl, wherein the N atom in the pyridinyl group may be in different positions;
or a pharmaceutically acceptable salt or acid addition salt, a racemic mixture, or its corresponding enantiomer and/or optical isomer and/or stereoisomer thereof, for example the following compounds:
3-[2,6-difluoro-4-(2-phenylethynyl)phenyl]-1-isopropyl-imidazolidine-2,4-dione
(5RS)-3-[2,6-difluoro-4-(2-phenylethynyl)phenyl]-1-isopropyl-5-methyl-imidazolidine-2,4-dione
3-[2,6-difluoro-4-(2-phenylethynyl)phenyl]-1-isopropyl-5,5-dimethyl-imidazolidine-2,4-dione
3-[2,6-difluoro-4-(2-phenylethynyl)phenyl]-5,5-dimethyl-1-phenyl-imidazolidine-2,4-dione
1-tert-butyl-3-[2,6-difluoro-4-(2-phenylethynyl)phenyl]imidazolidine-2,4-dione
1-cyclopropyl-3-[2,6-difluoro-4-(2-phenylethynyl)phenyl]imidazolidine-2,4-dione or
7-[2,6-difluoro-4-(2-phenylethynyl)phenyl]-5-isopropyl-2-oxa-5,7-diazaspiro[3.4]octane-6,8-dione.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises
a) reacting a compound of formula 3

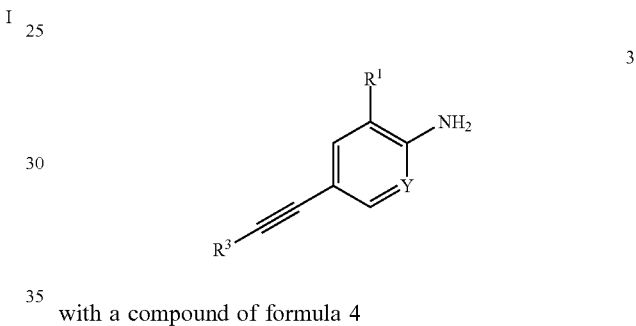

3 with a compound of formula 4

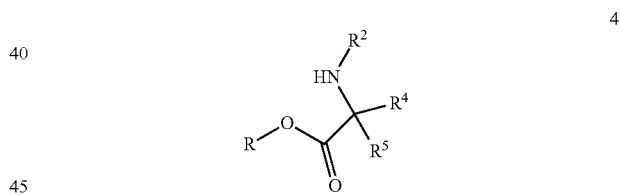

4 wherein R is methyl, ethyl or hydrogen and the other substituents are described above, with triphosgene or carbonyldiimidazole (CDI), in the presence or absence of a base, such as triethylamine, and in a solvent, such as toluene or dioxane, to a compound of formula

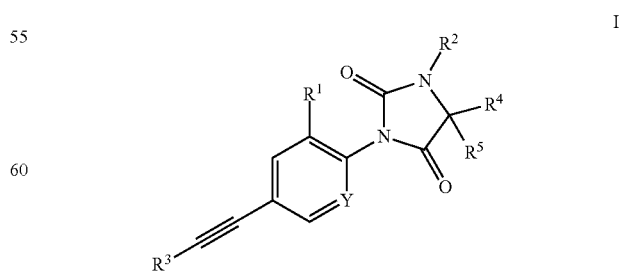

I and, if desired, converting the compound(s) obtained into pharmaceutically acceptable acid addition salt(s).

The preparation of compounds of formula I is further described in more detail in scheme 1 and in examples 1-13.

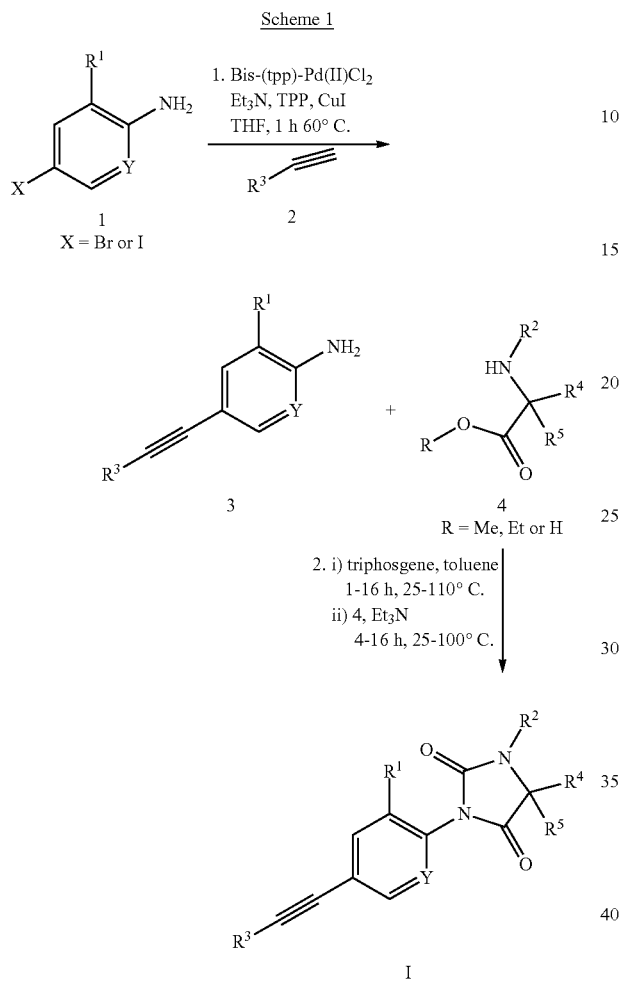

An ethynyl-phenyl, ethynyl-pyridyl substituted imidazolidine-2,4-dione compound of general formula I can be obtained for example by Sonogashira coupling of an appropriately substituted aniline or aminopyridine 1 with an appropriately substituted arylacetylene 2 to yield the desired ethynyl compounds of formula 3. Reacting ethynyl compounds of formula 3 with an appropriately substituted aminoester or aminoacid of formula 4 with phosgene or a phosgene equivalent such as triphosgene or carbonyldiimidazole (CDI) in presence or absence of a base such as triethylamine in a solvent such as toluene or dioxane forms the desired ethynyl-phenyl, ethynyl-pyridyl substituted imidazolidine-2,4-dione compound of general formula I (scheme 1). Introduction of the $R^2$ substituent can also be realized at various points in the synthetic sequence via alkylation of the corresponding intermediate where $R^2$=H.

Generally speaking, the sequence of steps used to synthesize the compounds of formula I can also be modified in certain cases.

BIOLOGICAL ASSAY AND DATA

Determination of $EC_{50}$ Values Using a Ca2+ Mobilization in vitro Assay on Recombinant Human mGlu4 Expressed in HEK293 Cells:

A monoclonal HEK-293 cell line stably transfected with a cDNA encoding for the human mGlu4 receptor was generated; for the work with mGlu4 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist (2S)-2-amino-4-phosphonobutanoic acid (L-AP4) was added to the cells at a concentration corresponding to $EC_{20}$ with on-line recording of fluorescence; in order to account for day-to-day variations in the responsiveness of cells, the $EC_{20}$ of L-AP4 was determined immediately ahead of each experiment by recording of a full dose-response curve of L-AP4.

Responses were measured as peak increase in fluorescence minus basal (i.e. fluorescence without addition of L-AP4), normalized to the maximal stimulatory effect obtained with saturating concentrations of L-AP4. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (drug concentration at which 50% of the maximal receptor activation was achieved), the Hill coefficient as well as the maximal response in % of the maximal stimulatory effect obtained with saturating concentrations of L-AP4 were calculated (see FIG. 1).

Positive signals obtained during the pre-incubation with the PAM test compounds (i.e. before application of an $EC_{20}$ concentration of L-AP4) were indicative of an agonistic activity, the absence of such signals were demonstrating the lack of agonistic activities. A depression of the signal observed after addition of the $EC_{20}$ concentration of L-AP4 was indicative of an inhibitory activity of the test compound.

List of Examples and Data:

| Ex. | Structure | Name | EC$_{50}$ (nM) mGlu4PAM | Eff. (%) |
|---|---|---|---|---|
| 1 | 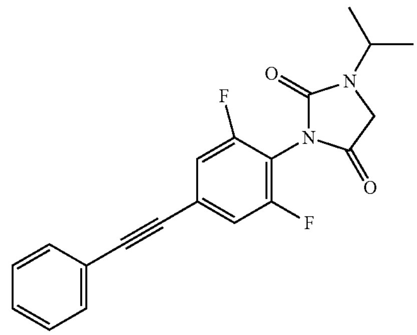 [SMILES: CC(C)N1CC(=O)N(c2c(F)cc(C#Cc3ccccc3)cc2F)C1=O] | 3-[2,6-Difluoro-4-(2-phenylethynyl)phenyl]-1-isopropyl-imidazolidine-2,4-dione | 441 | 154 |
| 2 | 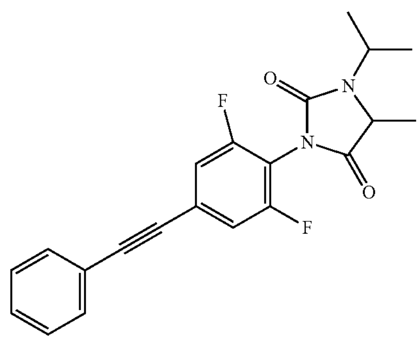 [SMILES: CC(C)N1C(=O)N(c2c(F)cc(C#Cc3ccccc3)cc2F)C(=O)C1C] | (5RS)-3-[2,6-Difluoro-4-(2-phenylethynyl)phenyl]-1-isopropyl-5-methyl-imidazolidine-2,4-dione | 104 | 107 |
| 3 | 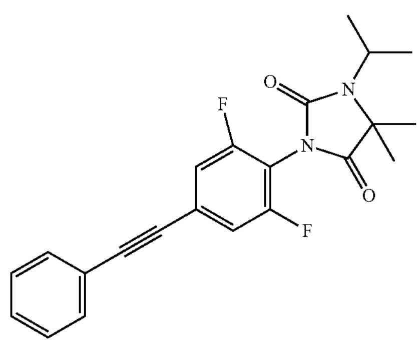 [SMILES: CC(C)N1C(=O)N(c2c(F)cc(C#Cc3ccccc3)cc2F)C(=O)C1(C)C] | 3-[2,6-Difluoro-4-(2-phenylethynyl)phenyl]-1-isopropyl-5,5-dimethyl-imidazolidine-2,4-dione | 286 | 98 |
| 4 | 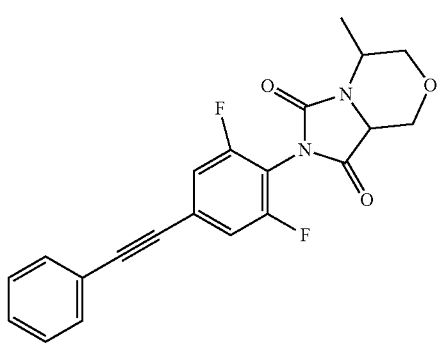 [SMILES: CC1COCC2C(=O)N(c3c(F)cc(C#Cc4ccccc4)cc3F)C(=O)N12] | (5RS,8aRS)-2-[2,6-Difluoro-4-(2-phenylethynyl)phenyl]-5-methyl-5,6,8,8a-tetrahydroimidazo[5,1-c][1,4]oxazine-1,3-dione | 204 | 188 |

-continued
| Ex. | Structure | Name | EC$_{50}$ (nM) mGlu4PAM | Eff. (%) |
|---|---|---|---|---|
| 5 | 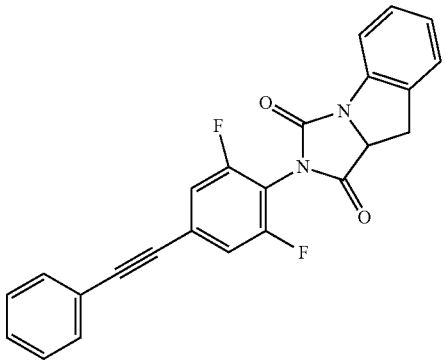 [SMILES: O=C1C2Cc3ccccc3N2C(=O)N1c1c(F)cc(C#Cc2ccccc2)cc1F] | (3aRS)-2-[2,6-Difluoro-4-(2-phenylethynyl)phenyl]-3a,4-dihydroimidazo[1,5-a]indole-1,3-dione | 188 | 103 |
| 6 | 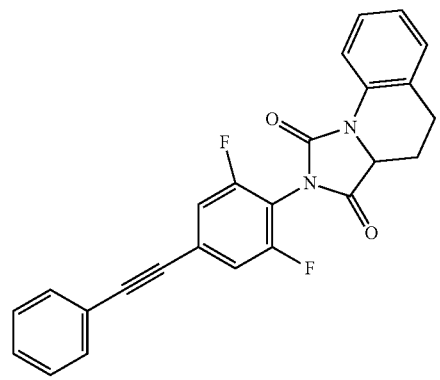 [SMILES: O=C1C2CCc3ccccc3N2C(=O)N1c1c(F)cc(C#Cc2ccccc2)cc1F] | (3aRS)-2-[2,6-Difluoro-4-(2-phenylethynyl)phenyl]-4,5-dihydro-3aH-imidazo[1,5-a]quinoline-1,3-dione | 74 | 110 |
| 7 | 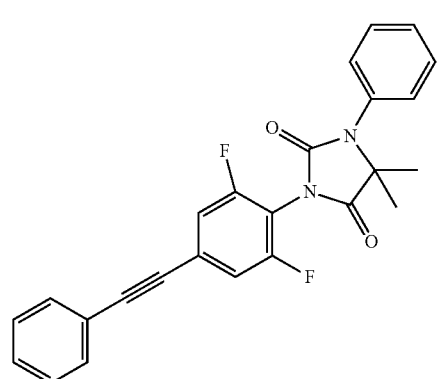 | 3-[2,6-Difluoro-4-(2-phenylethynyl)phenyl]-5,5-dimethyl-1-phenyl-imidazolidine-2,4-dione | 242 | 222 |
| 8 | 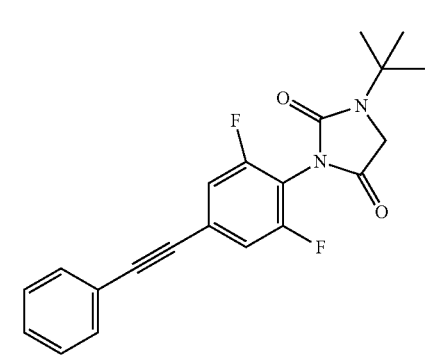 [SMILES: CC(C)(C)N1CC(=O)N(c2c(F)cc(C#Cc3ccccc3)cc2F)C1=O] | 1-tert-Butyl-3-[2,6-difluoro-4-(2-phenylethynyl)phenyl]imidazolidine-2,4-dione | 222 | 143 |

-continued

| Ex. | Structure | Name | EC$_{50}$ (nM) mGlu4PAM | Eff. (%) |
|---|---|---|---|---|
| 9 | 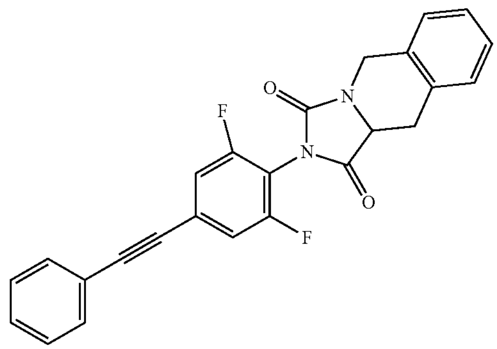 [SMILES: O=C1C2Cc3ccccc3CN2C(=O)N1c1c(F)cc(C#Cc2ccccc2)cc1F] | (10aRS)-2-[2,6-Difluoro-4-(2-phenylethynyl)phenyl]-10,10a-dihydro-5H-imidazo[1,5-b]isoquinoline-1,3-dione | 56 | 99 |
| 10 | 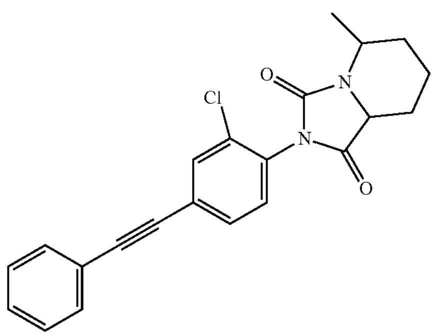 [SMILES: CC1CCCC2C(=O)N(c3ccc(C#Cc4ccccc4)cc3Cl)C(=O)N12] | (5RS,8aRS)-2-[2-Chloro-4-(2-phenylethynyl)phenyl]-5-methyl-6,7,8,8a-tetrahydro-5H-imidazo[1,5-a]pyridine-1,3-dione | 256 | 232 |
| 11 | 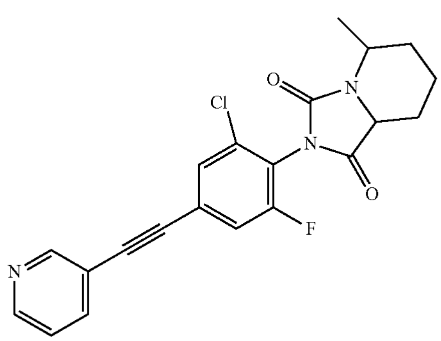 [SMILES: CC1CCCC2C(=O)N(c3c(F)cc(C#Cc4cccnc4)cc3Cl)C(=O)N12] | (5RS,8aRS)-2-[2-Chloro-6-fluoro-4-[2-(3-pyridyl)ethynyl]phenyl]-5-methyl-6,7,8,8a-tetrahydro-5H-imidazo[1,5-a]pyridine-1,3-dione | 180 | 140 |
| 12 | 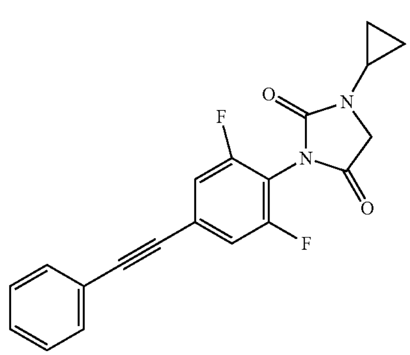 [SMILES: O=C1CN(C2CC2)C(=O)N1c1c(F)cc(C#Cc2ccccc2)cc1F] | 1-Cyclopropyl-3-[2,6-difluoro-4-(2-phenylethynyl)phenyl]imidazolidine-2,4-dione | 370 | 113 |

| Ex. | Structure | Name | EC$_{50}$ (nM) mGlu4PAM | Eff. (%) |
|---|---|---|---|---|
| 13 | 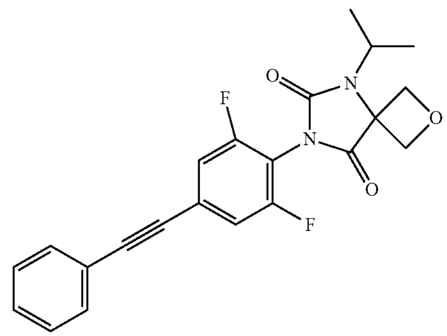 [SMILES: CC(C)N1C(=O)N(c2c(F)cc(C#Cc3ccccc3)cc2F)C(=O)C12COC2] | 7-[2,6-Difluoro-4-(2-phenylethynyl)phenyl]-5-isopropyl-2-oxa-5,7-diazaspiro[3.4]octane-6,8-dione | 230 | 100 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention:

Tablets of the following composition are produced in a conventional manner:

| mg/Tablet | |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXPERIMENTAL SECTION

Example 1

3-[2,6-Difluoro-4-(2-phenylethynyl)phenyl]-1-isopropyl-imidazolidine-2,4-dione

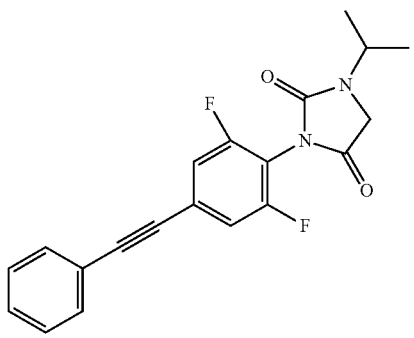 [SMILES: CC(C)N1CC(=O)N(c2c(F)cc(C#Cc3ccccc3)cc2F)C1=O]

Step 1: 2,6-Difluoro-4-phenylethynyl-phenylamine

Bis-(triphenylphosphine)-palladium(II)dichloride (826 mg, 1.18 mmol, 0.02 equiv.) was dissolved in 100 ml THF. 2,6-Difluoro-4-iodoaniline (15 g, 58.8 mmol) and phenylacetylene (7.2 g, 7.8 ml, 70.6 mmol, 1.2 equiv.) were added at room temperature. Triethylamine (29.8 g, 41 ml, 0.29 mol, 5 equiv.), triphenylphosphine (617 mg, 2.35 mmol, 0.04 equiv.) and copper(I)iodide (112 mg, 0.58 mmol, 0.01 equiv.) were added and the mixture was stirred for 1 hour at 60° C. The reaction mixture was cooled and extracted with saturated NaHCO$_3$ solution and two times with ethyl acetate. The organic layers were washed three times with water, dried over sodium sulfate and evaporated to dryness. The crude product was purified by flash chromatography on a silica gel column eluting with an ethyl acetate:heptane gradient 0:100 to 40:60. The desired 2,6-difluoro-4-phenylethynyl-phenylamine (12.6 g, 93% yield) was obtained as a yellow solid, MS: m/e=230.1 (M+H$^+$).

Step 2: 3-[2,6-Difluoro-4-(2-phenylethynyl)phenyl]-1-isopropyl-imidazolidine-2,4-dione 2,6-Difluoro-4-phenylethynyl-phenylamine (Example 1, step 1) (180 mg, 0.79 mmol) was dissolved in toluene (3.0 ml) and bis(trichloromethyl) carbonate (93 mg, 0.31 mmol, 0.4 equiv.) was added at room temperature. The mixture was stirred for 1 hour at 110° C. To the mixture Et$_3$N (397 mg, 0.55 ml, 3.93 mmol, 5 equiv.) and ethyl 2-(isopropylamino)acetate hydrochloride (171 mg, 0.94 mmol, 1.2 equiv.) were added and stirred for 16 hours at 110° C. The reaction mixture was cooled and loaded directly onto a silica gel column. The crude product was purified by flash chromatography eluting with an ethyl acetate:heptane gradient 0:100 to 60:40. The desired 3-[2,6-difluoro-4-(2-phenylethynyl)phenyl]-1-isopropyl-imidazolidine-2,4-dione (164 mg, 59% yield) was obtained as a white solid, MS: m/e=355.2 (M+H$^+$).

Example 2

(5RS)-3-[2,6-Difluoro-4-(2-phenylethynyl)phenyl]-1-isopropyl-5-methyl-imidazolidine-2,4-dione

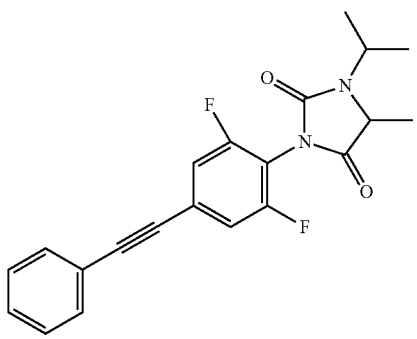 [SMILES: CC(C)N1C(=O)N(c2c(F)cc(C#Cc3ccccc3)cc2F)C(=O)C1C]

The title compound was obtained as a yellow oil, MS: m/e=369.2 (M+H$^-$), using chemistry similar to that described in Example 1, step 2 from 2,6-difluoro-4-phenylethynyl-phenylamine (Example 1, step 1) and 2-(isopropylamino)propanoic acid hydrochloride.

Example 3

3-[2,6-Difluoro-4-(2-phenylethynyl)phenyl]-1-isopropyl-5,5-dimethyl-imidazolidine-2,4-dione

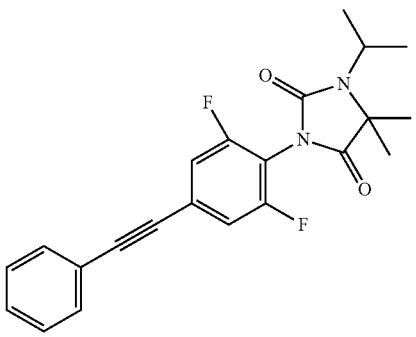 [SMILES: CC(C)N1C(=O)N(c2c(F)cc(C#Cc3ccccc3)cc2F)C(=O)C1(C)C]

The title compound was obtained as a light yellow oil, MS: m/e=383.2 (M+H$^+$), using chemistry similar to that described in Example 1, step 2 from 2,6-difluoro-4-phenylethynyl-phenylamine (Example 1, step 1) and methyl 2-(isopropylamino)-2-methylpropanoate.

Example 4

(5RS,8aRS)-2-[2,6-Difluoro-4-(2-phenylethynyl)phenyl]-5-methyl-5,6,8,8a-tetrahydroimidazo[5,1-c][1,4]oxazine-1,3-dione

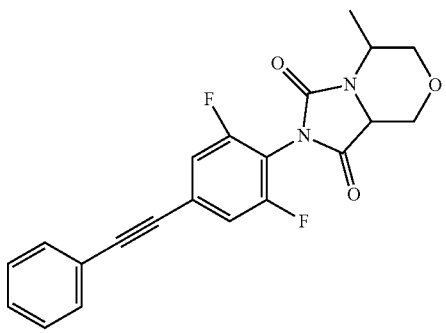 [SMILES: CC1COCC2C(=O)N(c3c(F)cc(C#Cc4ccccc4)cc3F)C(=O)N12]

The title compound was obtained as a white solid, MS: m/e=383.1 (M+H$^+$), using chemistry similar to that described in Example 1, step 2 from 2,6-difluoro-4-phenylethynyl-phenylamine (Example 1, step 1) and (3RS,5RS)-5-methylmorpholine-3-carboxylic acid.

Example 5

(3aRS)-2-[2,6-Difluoro-4-(2-phenylethynyl)phenyl]-3a,4-dihydroimidazo[1,5-a]indole-1,3-dione

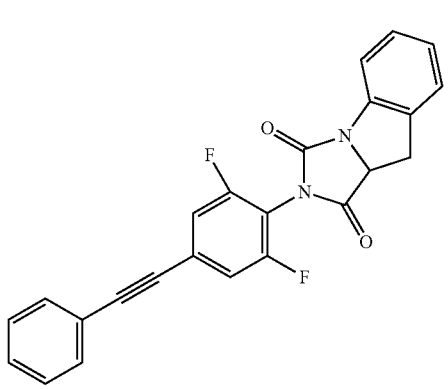 [SMILES: O=C1C2Cc3ccccc3N2C(=O)N1c1c(F)cc(C#Cc2ccccc2)cc1F]

The title compound was obtained as a light yellow solid, MS: m/e=401.3 (M+H⁺), using chemistry similar to that described in Example 1, step 2 from 2,6-difluoro-4-phenylethynyl-phenylamine (Example 1, step 1) and (2RS)-indoline-2-carboxylic acid.

Example 6

(3aRS)-2-[2,6-Difluoro-4-(2-phenylethynyl)phenyl]-4,5-dihydro-3aH-imidazo[1,5-a]quinoline-1,3-dione

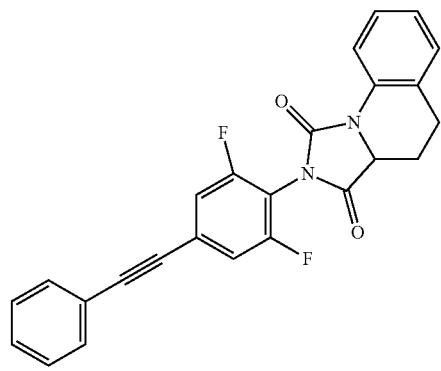 [SMILES: O=C1C2CCc3ccccc3N2C(=O)N1c1c(F)cc(C#Cc2ccccc2)cc1F]

The title compound was obtained as a white solid, MS: m/e=415.3 (M+H⁺), using chemistry similar to that described in Example 1, step 2 from 2,6-difluoro-4-phenylethynyl-phenylamine (Example 1, step 1) and methyl (2RS)-1,2,3,4-tetrahydroquinoline-2-carboxylate.

Example 7

3-[2,6-Difluoro-4-(2-phenylethynyl)phenyl]-5,5-dimethyl-1-phenyl-imidazolidine-2,4-dione

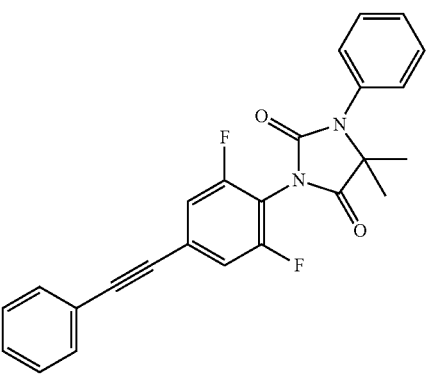 [SMILES: CC1(C)C(=O)N(c2c(F)cc(C#Cc3ccccc3)cc2F)C(=O)N1c1ccccc1]

The title compound was obtained as a light yellow solid, MS: m/e=417.2 (M+H⁺), using chemistry similar to that described in Example 1, step 2 from 2,6-difluoro-4-phenylethynyl-phenylamine (Example 1, step 1) and 2-methyl-2-(phenylamino)propanoic acid.

Example 8

1-tert-Butyl-3-[2,6-difluoro-4-(2-phenylethynyl)phenyl]imidazolidine-2,4-dione

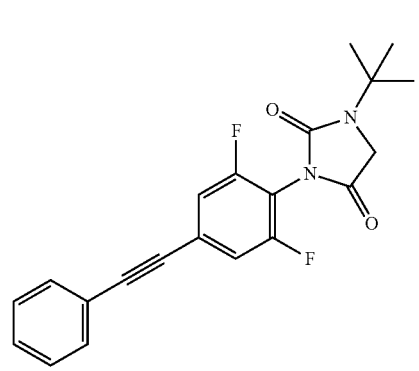 [SMILES: CC(C)(C)N1CC(=O)N(c2c(F)cc(C#Cc3ccccc3)cc2F)C1=O]

The title compound was obtained as a yellow oil, MS: m/e=369.2 (M+H⁻), using chemistry similar to that described in Example 1, step 2 from 2,6-difluoro-4-phenylethynyl-phenylamine (Example 1, step 1) and 2-(tert-butylamino)acetic acid hydrochloride.

Example 9

(10aRS)-2-[2,6-Difluoro-4-(2-phenylethynyl)phenyl]-10,10a-dihydro-5H-imidazo[1,5-b]isoquinoline-1,3-dione

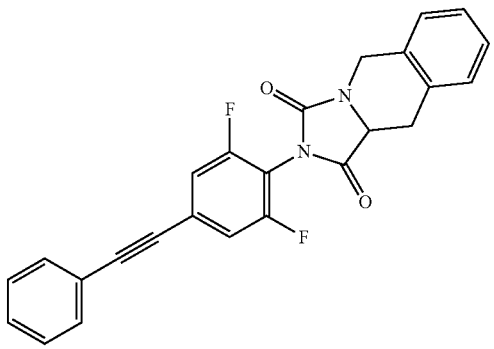 [SMILES: O=C1C2Cc3ccccc3CN2C(=O)N1c1c(F)cc(C#Cc2ccccc2)cc1F]

The title compound was obtained as a light yellow solid, MS: m/e=415.2 (M+H$^+$), using chemistry similar to that described in Example 1, step 2 from 2,6-difluoro-4-phenylethynyl-phenylamine (Example 1, step 1) and methyl (3RS)-1,2,3,4-tetrahydroisoquinoline-3-carboxylic acid.

Example 10

(5RS,8aRS)-2-[2-Chloro-4-(2-phenylethynyl)phenyl]-5-methyl-6,7,8,8a-tetrahydro-5H-imidazo[1,5-a]pyridine-1,3-dione

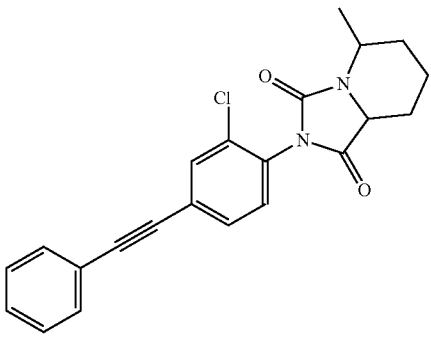 [SMILES: CC1CCCC2C(=O)N(c3ccc(C#Cc4ccccc4)cc3Cl)C(=O)N12]

Step 1: 2-Chloro-4-(2-phenylethynyl)aniline

The title compound was obtained as a yellow solid, MS: m/e=228.1/230.1 (M+H$^+$), using chemistry similar to that described in Example 1, step 1 from 2-chloro-4-iodoaniline and phenylacetylene.

Step 2: (5RS,8aRS)-2-[2-Chloro-4-(2-phenylethynyl)phenyl]-5-methyl-6,7,8,8a-tetrahydro-5H-imidazo[1,5-a]pyridine-1,3-dione The title compound was obtained as a white solid, MS: m/e=379.2/381.2 (M+H$^-$), using chemistry similar to that described in Example 1, step 2 from 2-chloro-4-(2-phenylethynyl)aniline (Example 10, step 1) and methyl (2RS,6RS)-6-methylpiperidine-2-carboxylate.

Example 11

(5RS,8aRS)-2-[2-Chloro-6-fluoro-4-[2-(3-pyridyl)ethynyl]phenyl]-5-methyl-6,7,8,8a-tetrahydro-5H-imidazo[1,5-a]pyridine-1,3-dione

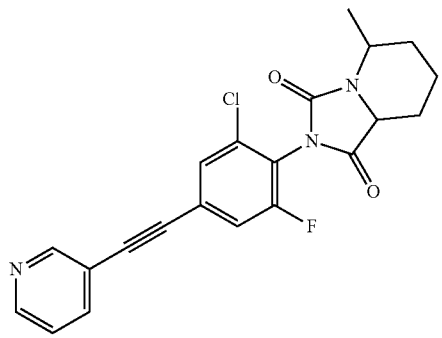 [SMILES: CC1CCCC2C(=O)N(c3c(F)cc(C#Cc4cccnc4)cc3Cl)C(=O)N12]

Step 1:
2-Chloro-6-fluoro-4-[2-(3-pyridyl)ethynyl]aniline

The title compound was obtained as a yellow solid, MS: m/e=228.1/230.1 (M+H$^+$), using chemistry similar to that described in Example 1, step 1 from 4-bromo-2-chloro-6-fluoro-aniline and 3-ethynylpyridine.

Step 2: (5RS,8aRS)-2-[2-Chloro-4-(2-phenylethynyl)phenyl]-5-methyl-6,7,8,8a-tetrahydro-5H-imidazo[1,5-a]pyridine-1,3-dione The title compound was obtained as a white solid, MS: m/e=398.0/400.0 (M+H$^-$), using chemistry similar to that described in Example 1, step 2 from 2-chloro-6-fluoro-4-[2-(3-pyridyl)ethynyl]aniline (Example 11, step 1) and methyl (2RS,6RS)-6-methylpiperidine-2-carboxylate.

Example 12

1-Cyclopropyl-3-[2,6-difluoro-4-(2-phenylethynyl)phenyl]imidazolidine-2,4-dione

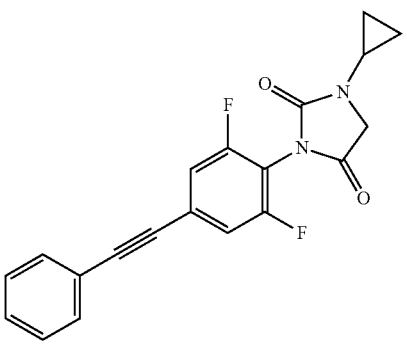 [SMILES: O=C1CN(C2CC2)C(=O)N1c1c(F)cc(C#Cc2ccccc2)cc1F]

The title compound was obtained as a white solid, MS: m/e=353.1 (M+H$^+$), using chemistry similar to that described in Example 1, step 2 from 2,6-difluoro-4-phenylethynyl-phenylamine (Example 1, step 1) and 2-(cyclopropylamino)acetic acid.

Example 13

7-[2,6-Difluoro-4-(2-phenylethynyl)phenyl]-5-isopropyl-2-oxa-5,7-diazaspiro[3.4]octane-6,8-dione

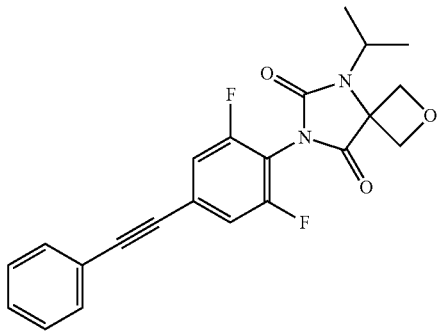 [SMILES: CC(C)N1C(=O)N(c2c(F)cc(C#Cc3ccccc3)cc2F)C(=O)C12COC2]

Step 1: 7-[2,6-Difluoro-4-(2-phenylethynyl)phenyl]-2-oxa-5,7-diazaspiro[3.4]octane-6,8-dione The title compound was obtained as a light yellow solid, MS: m/e=353.2 (M+H$^+$), using chemistry similar to that described in Example 1, step 2 from 2,6-difluoro-4-phenylethynyl-phenylamine (Example 1, step 1) and methyl 3-aminooxetane-3-carboxylate.

Step 2: 7-[2,6-Difluoro-4-(2-phenylethynyl)phenyl]-5-isopropyl-2-oxa-5,7-diazaspiro[3.4]octane-6,8-dione (60 mg, 169 μmol) 7-[2,6-Difluoro-4-(2-phenylethynyl)phenyl]-2-oxa-5,7-diazaspiro[3.4]octane-6,8-dione (Example 13, step 1) was dissolved in DMF (1 ml) and cesium carbonate (110 mg, 0.34 mmol, 2 equiv.) and 2-iodopropane (58 mg, 34 μl, 0.34 mmol, 2 equiv.) were added at room temperature. The mixture was stirred for 4 hours at room temperature. The reaction mixture was cooled and extracted with saturated NaHCO$_3$ solution and two times with ethyl acetate. The organic layers were washed with water and brine, dried over sodium sulfate and evaporated to dryness. The crude product was purified by flash chromatography on a silica gel column eluting with an ethyl acetate:heptane gradient 0:100 to 60:40. The desired 7-[2,6-difluoro-4-(2-phenylethynyl)phenyl]-5-isopropyl-2-oxa-5,7-diazaspiro[3.4]octane-6,8-dione (34 mg, 51% yield) was obtained as a white solid, MS: m/e=397.2 (M+H$^+$).

The invention claimed is:

1. A compound of formula I

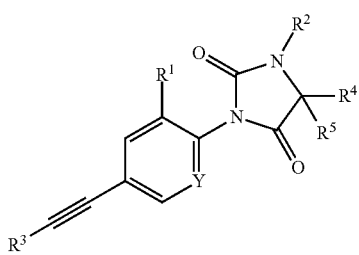

I wherein
Y is C—R$^{1'}$;
R$^{1'}$ is hydrogen or halogen;
R$^1$ is hydrogen or halogen;
R$^2$ is hydrogen, lower alkyl or phenyl;
R$^4$ is hydrogen or lower alkyl;
or R$^2$ and R$^4$ may form together with the corresponding atoms, to which they are attached the following rings

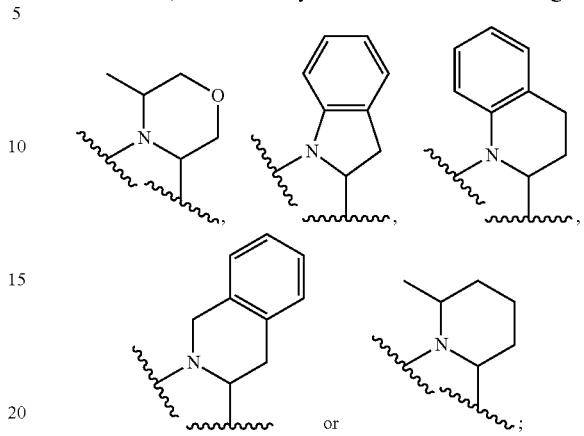

R$^5$ is hydrogen or lower alkyl; and if R$^2$ and R$^4$ form a ring as described above, than R$^5$ is hydrogen; or
R$^4$ and R$^5$ may form together with the C-atom to which they are attached a heterocycloalkyl ring;
R$^3$ is phenyl or pyridinyl, wherein the N atom in the pyridinyl group may be in different positions;
or a pharmaceutically acceptable salt or acid addition salt, a racemic mixture, or its corresponding enantiomer and/or optical isomer and/or stereoisomer thereof.

2. A compound of formula I according to claim 1,

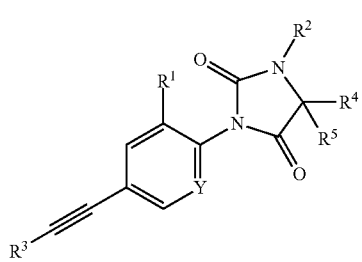

I wherein
Y is C—R$^{1'}$;
R$^{1'}$ is hydrogen or halogen;
R$^1$ is hydrogen or halogen;
R$^2$ is hydrogen, lower alkyl or phenyl;
R$^4$ is hydrogen or lower alkyl;
R$^5$ is hydrogen or lower alkyl; or
R$^4$ and R$^5$ may form together with the C-atom to which they are attached a heterocycloalkyl ring;
R$^3$ is phenyl or pyridinyl, wherein the N atom in the pyridinyl group may be in different positions;
or a pharmaceutically acceptable salt or acid addition salt, a racemic mixture, or its corresponding enantiomer and/or optical isomer and/or stereoisomer thereof.

3. A compound of formula I according to claim 1, wherein the compound is
3-[2,6-difluoro-4-(2-phenylethynyl)phenyl]-1-isopropyl-imidazolidine-2,4-dione
(5RS)-3-[2,6-difluoro-4-(2-phenylethynyl)phenyl]-1-isopropyl-5-methyl-imidazolidine-2,4-dione
3-[2,6-difluoro-4-(2-phenylethynyl)phenyl]-1-isopropyl-5,5-dimethyl-imidazolidine-2,4-dione 3-[2,6-difluoro-4-(2-phenylethynyl)phenyl]-5,5-dimethyl-1-phenyl-imidazolidine-2,4-dione 1-tert-butyl-3-[2,6-difluoro-4-(2-phenylethynyl)phenyl]imidazolidine-2,4-dione 1-cyclopropyl-3-[2,6-difluoro-4-(2-phenylethynyl)phenyl]imidazolidine-2,4-dione or 7-[2,6-difluoro-4-(2-phenylethynyl)phenyl]-isopropyl-2-oxa-5,7-diazaspiro[3.4]octane-6,8-dione.

4. A compound of formula I according to claim 1,

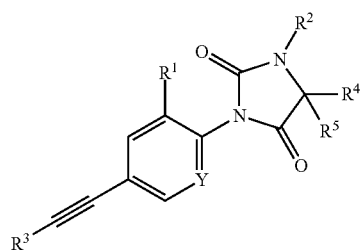

wherein
Y is C—R¹';
R¹' is hydrogen or halogen;
R¹ is hydrogen or halogen;
R² and R⁴ form together with the corresponding atoms to which they are attached the following rings

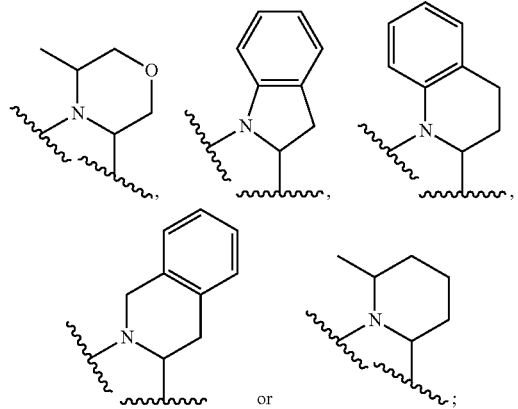

R⁵ is hydrogen or
R⁴ and R⁵ may form together with the C-atom to which they are attached a heterocycloalkyl ring;
R³ is phenyl or pyridinyl, wherein the N atom in the pyridinyl group may be in different positions;
or a pharmaceutically acceptable salt or acid addition salt, a racemic mixture, or its corresponding enantiomer and/or optical isomer and/or stereoisomer thereof.

5. A compound of formula I according to claim 1, wherein the compound is (5RS,8aRS)-2-[2,6-difluoro-4-(2-phenylethynyl)phenyl]-5-methyl-5,6,8,8a-tetrahydroimidazo[5,1-c][1,4]oxazine-1,3-dione (3aRS)-2-[2,6-difluoro-4-(2-phenylethynyl)phenyl]-3a,4-dihydroimidazo[1,5-a]indole-1,3-dione (3aRS)-2-[2,6-difluoro-4-(2-phenylethynyl)phenyl]-4,5-dihydro-3aH-imidazo[1,5-a]quinoline-1,3-dione (10aRS)-2-[2,6-difluoro-4-(2-phenylethynyl)phenyl]-10,10a-dihydro-5H-imidazo[1,5-b]isoquinoline-1,3-dione (5RS,8aRS)-2-[2-chloro-4-(2-phenylethynyl)phenyl]-5-methyl-6,7,8,8a-tetrahydro-5H-imidazo[1,5-a]pyridine-1,3-dione or (5RS,8aRS)-2-[2-chloro-6-fluoro-4-[2-(3-pyridyl)ethynyl]phenyl]-5-methyl-6,7,8,8a-tetrahydro-5H-imidazo[1,5-a]pyridine-1,3-dione.

6. A method of preparing a compound of formula I as defined in claim 1, comprising:
reacting a compound of formula 3

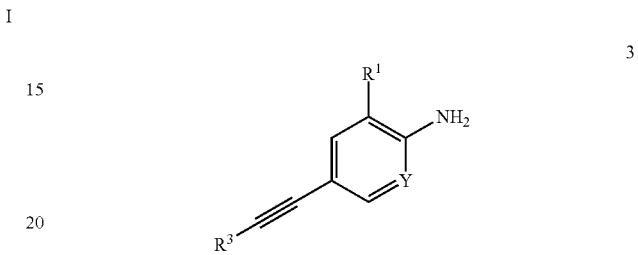

with a compound of formula 4

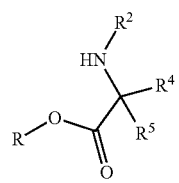

wherein R is methyl, ethyl or hydrogen, and the other substituents are described above, with triphosgene or carbonyldiimidazole (CDI), in the presence or absence of a base, selected from triethylamine, and in a solvent, selected from toluene or dioxane, to a compound of formula

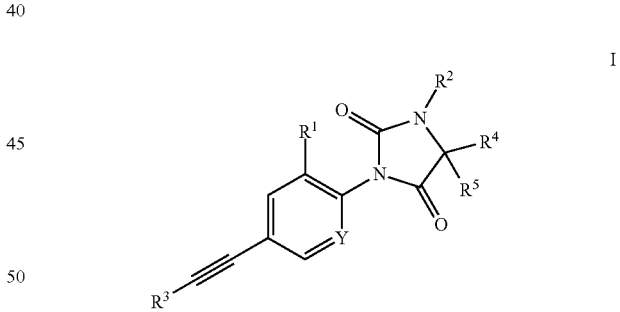

and, if desired, converting the compound obtained into a pharmaceutically acceptable acid addition salt.

7. A pharmaceutical composition comprising a compound of formula I according to claim 1 and a pharmaceutically acceptable excipient.

8. A method for the treatment of Parkinson's disease, anxiety, emesis, obsessive compulsive disorder, autism, neuroprotection, prostate cancer, colorectal cancer, depression, schizophrenia and diabetes type 2 of a patient, which method comprises administering an effective amount to the patient of a compound of formula I according to claim 1.

* * * * *